US012582477B2

(12) United States Patent
Birkhold et al.

(10) Patent No.: US 12,582,477 B2
(45) Date of Patent: Mar. 24, 2026

(54) COMPUTER-IMPLEMENTED METHOD FOR DETERMINATION OF A BONE CEMENT VOLUME OF A BONE CEMENT FOR A PERCUTANEOUS VERTEBROPLASTY

(71) Applicant: Siemens Healthcare GmbH, Erlangen (DE)

(72) Inventors: Annette Birkhold, Stuttgart (DE); Alois Regensburger, Poxdorf (DE)

(73) Assignee: Siemens Healthineers AG, Forchheim (DE)

( * ) Notice: Subject to any disclaimer, the term of this patent is extended or adjusted under 35 U.S.C. 154(b) by 297 days.

(21) Appl. No.: 18/228,196

(22) Filed: Jul. 31, 2023

(65) Prior Publication Data

US 2024/0041527 A1     Feb. 8, 2024

(30) Foreign Application Priority Data

Aug. 3, 2022     (DE) ..................... 10 2022 208 023.8

(51) Int. Cl.
A61B 34/10 (2016.01)
G06T 7/00 (2017.01)

(52) U.S. Cl.
CPC ............ A61B 34/10 (2016.02); G06T 7/0012 (2013.01); *G06T 2207/10081* (2013.01); *G06T 2207/30012* (2013.01)

(58) Field of Classification Search
None
See application file for complete search history.

(56) References Cited

U.S. PATENT DOCUMENTS

2014/0364807 A1     12/2014     Couture et al.
2019/0254750 A1     8/2019     Metz

FOREIGN PATENT DOCUMENTS

CN     114145835 A     3/2022
DE     102017221280 A1     5/2019
EP     3120796 A1     1/2017

(Continued)

OTHER PUBLICATIONS

Bukas et al; Patient-specific virtual spine straightening and vertebra inpainting: An automatic framework for osteoplasty planning; Mar. 23, 2021.*

(Continued)

*Primary Examiner* — Fan Zhang
(74) *Attorney, Agent, or Firm* — Lempia Summerfield Katz LLC

(57) ABSTRACT

The disclosure relates to a computer-implemented method for determination of a bone cement volume of a bone cement for a percutaneous vertebroplasty, which reduces complications due to the information provided by the method. The computer-implemented method includes: reading in or receiving data about a bone structure of a bone section; determining a bone density distribution of the bone section depending on the data; determining a bone space in the bone section depending on the determined bone density distribution, wherein a bone density of the bone space is less than a predetermined density threshold value; determining a bone space volume of the determined bone space; and determining and outputting the bone cement volume depending on the determined bone space volume.

17 Claims, 5 Drawing Sheets

(56)  References Cited

FOREIGN PATENT DOCUMENTS

EP        3007641  B1      8/2020
KR   100469086  B1  *   1/2005

OTHER PUBLICATIONS

Landgraf et al; Modelling and simulation of acrylic bone cement injection and curing within the framework of vertebroplasty; Feb. 8 2015.*
Liebschner et al; Effects of Bone Cement Volume and Distribution on Vertebral Stiffness After Vertebroplasty; Nov. 14, 2001.*

* cited by examiner

S6

S7

S8

S9

S10

S11

9

11

10

COMPUTER-IMPLEMENTED METHOD FOR DETERMINATION OF A BONE CEMENT VOLUME OF A BONE CEMENT FOR A PERCUTANEOUS VERTEBROPLASTY

The present patent document claims the benefit of German Patent Application No. 10 2022 208 023.8, filed Aug. 3, 2022, which is hereby incorporated by reference in its entirety.

TECHNICAL FIELD

The disclosure relates to a computer-implemented method for determination of a bone cement volume of a bone cement for a percutaneous vertebroplasty.

BACKGROUND

The metastatic spread of tumors in the bones, such as in the spinal column, causes serious neurological problems due to severe pain, spinal column fractures, and compression of the nerve roots and of the spinal column by the lesion mass. The ablation of spine metastases primarily serves to alleviate the pain and for tumor cavitation before the stabilization. Depending on the size and location of the lesion, a percutaneous vertebroplasty is frequently carried out after the ablation, because the strength of the spinal column is adversely affected.

In the vertebroplasty a viscose bone cement, as a rule polymethyl methacrylate (PMMA), is injected percutaneously into a fractured spinal column. In the metastasized spinal column, in up to 85.7% of all interventions, there have been reports after the vertebroplasty about leakages of the bone cement, wherein in 10% of the cases a leakage into the spinal canal was established.

Bone cement leakages may occur in various ways. Bone cement may escape along the rear vertebral venal plexus of the spinal column into the vertebral basal vein at the rear edge of the spinal column. A leakage may also occur with the interruption of the bone cortex of the spinal column, wherein the interruption of the cortical continuity of the spinal column is a risk factor für a leakage. With a continuous interruption of the spinal cortex, the bone cement may escape into the spinal canal and the nerve root canal, which leads to nerve damage and the corresponding symptoms. When bone cement escapes in this way, it has been established that the injection of a small amount of viscous bone cement at the corticalis fracture, a pause of a few seconds and the continuation of the cement injection after the blocking of the corticalis fracture may reduce the risk of an escape.

When hardened bone cement is injected in such a way that it exerts significant additional pressure or forces on additional spinal surfaces, pathological fractures are frequently the consequence. The success of the method, of which the primary aim is pain reduction and additional mobility of the patient at the palliative stage, is diminished or even made worse.

The critical variable, which may be decisive for the success or failure of the percutaneous vertebroplasty, is the volume of the bone cement injected into the bone. Currently, the doctor performing the operation determines the volume based on his or her experience. In case of doubt, bone screws are therefore used in order to additionally stabilize the bones. This requires an additional invasive intervention into a patient however, as well as costs and treatment time and is associated with an additional risk of complications.

SUMMARY AND DESCRIPTION

The underlying object of the disclosure is thus to provide a precise value of a bone cement volume for the percutaneous vertebroplasty, which may be determined based on data and independently of the experience of the doctor performing the operation.

The scope of the present disclosure is defined solely by the appended claims and is not affected to any degree by the statements within this summary. The present embodiments may obviate one or more of the drawbacks or limitations in the related art.

A first aspect of the disclosure is a computer-implemented method for determination of a bone cement volume of a bone cement for a percutaneous vertebroplasty. The computer-implemented method includes: reading in or receiving data about a bone structure of a bone section; determining a bone density distribution of the bone section depending on the data; determining a bone space in the bone section depending on the bone density distribution determined, wherein a bone density of the bone space is lower than a predetermined density threshold value; determining a bone space volume of the bone space determined; and determining and outputting the bone cement volume depending on the bone space volume determined.

The method may be carried out automatically on a computer, for example.

The bone section may refer to a section of a human bone or an animal bone. The bone section may include an entire bone, a part of a bone, or a number of neighboring bones. The bone section may be a vertebra, a part of a vertebra, or a number of neighboring vertebrae of a spinal column. The bone section may likewise also be understood as a section of a hip bone.

In particular, a value for the bone cement volume is determined and output by the method. To this end, the data about the bone structure is provided to the method, for example, on an electronic storage medium.

A bone structure may be understood as the inner structure of a bone, in particular the structure of the skeleton and of the bone marrow.

The data may be stored in the form of files and provide information about the bone structure. This data may be provided by a suitable measurement method or by an imaging method, for example, x-ray or Magnetic Resonance Tomography (MRT). In particular, the data may be obtained at a time preceding the method from a real bone section that is to be treated by the percutaneous vertebroplasty.

One form of embodiment makes provision for the data read in to include a computed tomography scan of the bone section. The computed tomography scan is in particular an image, (e.g., a three-dimensional, digital image), which may be created by Computed Tomography (CT) of the real bone section. The computed tomography scan may be created by high-resolution Cone Beam Computer Tomography (CBCT) or Digital Volume Tomography (DVT). The CT image may thus graphically represent the bone structure of the bone section as a high-resolution and three-dimensional image. The data may correspond to image data of the bone section and may be provided and read in as a stored image file or image files.

In one act, the bone density distribution of the bone section may be determined depending on the data. For example, the data may already contain values and/or information of the bone density distribution. The bone density distribution may be computed from the data read in. In particular, a computation of a volumetric bone density may be carried out by a distance transformation of the bone structure in order to determine the bone density distribution.

In particular, the bone density distribution may include data about a local, three-dimensional distribution of the bone density of the bone section. For example, the bone section may be divided into a plurality of three-dimensional bone elements, wherein each bone element of the plurality of three-dimensional bone elements is assigned a bone density.

Subsequently, the bone space may be determined that has a bone density less than the predetermined density threshold value. For example, those bone elements of the bone section that have a lower density assigned to them than the density threshold value may be grouped into the bone space.

The density threshold value may be defined or predetermined as a value beforehand. The density threshold value may be a value below which a stable bone structure is not given or above which a stable bone structure is given.

In particular, the bone space, (e.g., its local positioning and geometrical embodiment in the bone structure), may be output. For example, the bone space may be represented as a marked space of the computed tomography scan and displayed on a screen or output as an image file.

In an additional act, the bone space volume of the determined bone space may be determined. For example, the bone space volume of the bone space may be computed or measured. In particular, a value of the bone space volume is output.

Subsequently, depending on the bone space volume determined, the bone cement volume, in particular the value of the bone cement volume, is determined and output, (e.g., as a numerical value), wherein the numerical value may be output on a screen and/or stored in a file on a storage medium. Over and above, this a bone cement weight may be determined via a known bone cement density and output.

The advantage produced by the disclosure is that the bone cement volume is based on data about the bone structure and may be determined automatically based on this data. The bone cement volume determined may support the doctor performing the operation, in this case in injecting neither too much nor too little bone cement into the bone section. Through this, on the one hand a risk of a leakage due to too much injected bone cement is markedly reduced. Thus, a patient suffering because of the leakage may be prevented. Likewise the risk is reduced of the bone still being too unstable due to too little injected bone cement even after the percutaneous vertebroplasty. This may mean that bone screws in the bone section may be dispensed with. Thus, an additional invasive intervention at the patient may be avoided. This lowers the treatment costs, the treatment time and reduces the risk of complications.

What is more, the bone space determined, and the associated bone space volume may be used as a basis for an ablation. The advantage is that the ablation may be planned and carried out precisely based on the data.

One form of embodiment makes provision for the bone cement volume determined to correspond to the bone space volume. This represents an especially simple option for determining the bone cement volume. This advantageously enables the risk to be reduced that too much or too little bone cement volume is injected.

An alternate form of embodiment makes provision for the determination of the bone cement volume, depending on the bone space volume determined, to include: processing the computed tomography (CT) scan, in that the bone space of the bone section determined is filled virtually, at least in part, with a first volume of the bone cement; determining a bone strength of the bone section virtually filled with the first volume of the bone cement; determining a first volume as bone cement volume when the bone strength determined fulfills a condition; and adjusting the first volume and repeating the acts of processing, determining the bone strength, and determining the first volume when the bone strength determined does not fulfill the condition.

In other words, the at least partly filled bone space may be quasi simulated on a computer.

In particular, before the at least part filling, an ablation of the bone space or a bone space exposed by the ablation may be simulated. In particular, there may be provision for a bone space volume to be changed by a simulated ablation, e.g., enlarged.

The first volume may be less than or equal to the bone space volume determined or the bone space volume changed by the simulated ablation.

Subsequently, the bone strength of the bone section filled virtually with the first volume of the bone cement is determined based on the bone section filled virtually.

The bone strength may be a single value and/or a bone strength distribution of the bone section. In particular, the bone strength distribution may include data about a local, three-dimensional distribution of the bone strength of the bone section.

For example, the bone strength may be determined by a simulation. In particular, the bone strength may be computed by a Finite Element Method (FEM). For this, a predetermined, virtual stress on the bone part, (e.g., in the form of forces and/or moments), may be selected as boundary condition for the FEM computation. One solution of the FEM computation may be a stress and/or a strain or their three-dimensional distribution, so that the bone strength may be determined based on the solution of the FEM computation.

As an alternative, there may be provision for the bone strength to be determined by an algorithm, for example, by machine learning (ML).

The first volume is determined as the bone cement volume when the bone strength determined fulfills a condition. The condition may be predetermined. The condition may be a threshold value or a range for a bone strength. If this condition is not fulfilled, the first volume is not selected as the bone cement volume, but act i. is carried out.

In an act, the first volume is adjusted, for example, enlarged or reduced. The adjusted first volume may correspond to a second volume of the bone cement, wherein the method acts of processing the CT scan, the determining of the bone strength, the determining of the first volume, and the adjusting of the first volume are repeated based on the second volume when the bone strength determined does not fulfill the condition.

Where the bone strength of the bone section filled with the second volume fulfills the condition, the second volume is determined as the bone cement volume.

Where the bone strength of the bone section filled with the second volume does not fulfill the condition, the second volume is changed. The adjusted second volume may correspond to a third volume of the bone cement, wherein the method acts of processing the CT scan, the determining of the bone strength, the determining of the first volume, and the adjusting of the first volume are repeated based on the third volume.

The method acts of processing the CT scan, the determining of the bone strength, the determining of the first volume, and the adjusting of the first volume may be repeated any number of times in this case until the bone strength fulfills the condition. In particular the method acts of processing the CT scan, the determining of the bone strength, the determining of the first volume, and the adjusting of the first volume may correspond to an iterative method for determination of the bone cement volume.

Should the condition not be fulfilled even after a plurality of repetitions there may be provision for the method acts of processing the CT scan, the determining of the bone strength, the determining of the first volume, and the adjusting of the first volume to be aborted after a specific number of repetitions. For example, the value of the volume is then output that comes closest to the value for fulfilling the condition.

The determination of the bone cement volume based on the condition to be fulfilled has the advantage that not only is the risk of a leakage reduced, but over and above this the bone cement volume may be determined based on the bone strength. Thus an optimal bone strength may be achieved, which may have an especially positive effect on the strength of the bone section.

One form of embodiment makes provision for the bone strength to be determined by machine learning (ML). In particular, the bone section filled virtually may be read in as the input variable for a trained ML model, wherein the bone strength of the bone section read in may be determined as the output variable.

The determination of the bone hardness by ML has the advantage that the determination does not have to be undertaken by complex and time-consuming computations. By contrast, a functioning ML model may determine the bone strength significantly more quickly, e.g., in a few seconds. The automated method is greatly speeded up and simplified by this. Savings may likewise be made in computing capacity.

One form of embodiment makes provision that, for determination of the bone strength by ML, an encoder architecture, or an encoder-decoder architecture of an artificial neural network (ANN) is used.

A first component of the encoder-decoder architecture may be an encoder. This may take a sequence of variable length as an input variable and convert this into a state with a fixed form. The second component is a decoder. The decoder may map the coded state of a fixed form to a variable length sequence as an output variable.

In this case, the encoder-decoder architecture of the artificial neural network may have as its input variable the bone section filled virtually. The encoder may convert this into a value of the bone strength. The decoder for its part may map the bone strength into a bone strength distribution of the bone section.

The encoder architecture may consequently determine the value of the bone strength. The encoder architecture however has the advantage that a computing overhead is greatly reduced compared to an encoder-decoder architecture. It may also be that the value of the bone strength may be sufficient for determining the bone cement volume.

The advantage of the encoder-decoder architecture, on the other hand, is that not just the value but the bone strength distribution may be determined. Although the computing effort is increased by comparison, the bone cement volume may be determined in a more targeted manner under some circumstances.

One form of embodiment makes provision for the artificial neural network to be trained with a plurality of computer tomographic images of bone parts and associated, numerically-computed solution of bone part strengths.

A bone part and the bone section may in particular have the same meaning and/or the same properties but are referred to differently for terminological distinction. The same applies for the computed tomography scan and the computed tomography image.

In particular, the plurality of computed tomography images may be provided as the input variable for the training. In particular, the numerically computed solutions may be compared for training purposes with the output variables of the ANN to be trained, after which the ANN may be trained by a training algorithm.

The numerically computed solutions may be computed beforehand by a FE method or the like.

One form of embodiment makes provision for the condition to be fulfilled when the bone strength determined corresponds to or exceeds a predetermined minimum strength value. The first volume may be adjusted in that the first volume is enlarged. The minimum strength value may be a value below which the bone section is solid or stiff enough to be stable. The minimum strength value may be predetermined. This has the advantage that the risk of a bone strength that is too low after an injection of the bone cement may be reduced.

An alternate form of embodiment makes provision for the condition to be fulfilled when the bone strength determined lies within a predetermined strength range. The first volume may be adjusted, wherein the first volume is reduced if the strength range is exceeded. Alternatively, the first volume may be adjusted, wherein the first volume is increased if the value is below the strength range.

The strength range may be a range in which the bone section is solid or stiff enough to be stable, and at the same time is elastic enough so that the risk of a fracture of the bone section is not increased. In particular, a lower value of the strength range may correspond to the minimum strength value, and also an upper value of the strength range may correspond to a maximum strength value.

This has the advantage that both a risk of an unstable bone section after the percutaneous vertebroplasty due to too little bone cement, and also a risk of a bone section susceptible to fractures may be significantly reduced. This enables a healing process to be speeded up and time and costs for the treatment to be reduced.

One form of embodiment makes provision, in the processing of the scan, before the virtual filling, for a bone substance in the bone space volume to be removed at least in part by a virtual ablation.

In other words, an ablation of the bone substance may be simulated. In a real intervention, the ablation may be a necessary intervention before a percutaneous vertebroplasty. By this intervention also being simulated beforehand particular, the real intervention in humans may be planned more precisely, the bone cement volume determined more accurately, and risk estimated even better.

In particular, it may be that the bone space volume is enlarged due to the ablation. The enlarged bone space volume may be employed for carrying out the determining of the bone space volume and/or the processing of the scan.

One form of embodiment makes provision, in the determination of the bone space, for a plurality of bone elements with a bone density less than the predetermined density threshold value to be determined. The plurality of bone elements may be grouped into the bone space, so that an envelope of the bone space is smoothed and/or convex.

In other words, the bone section may be divided into a plurality of three-dimensional bone elements, wherein each bone element of the plurality of three-dimensional bone elements is assigned an associated bone density. Subsequently, in the determining of the bone space, an intermediate sum may be formed by summing or grouping of the bone elements with bone elements that have a bone density lower than the predetermined density threshold value. This intermediate sum may have a non-smooth or angular surface. The bone space may now be formed based on the intermediate sum, by the surface of the intermediate sum being smoothed, so that the envelope of the bone space is smoothed and/or convex.

This has the advantage that the bone space may represent a realistic bone space for the real percutaneous vertebroplasty. This enables the intervention to be planned more exactly, the bone cement volume to be determined more precisely and treatment risks to be reduced.

One form of embodiment makes provision, depending on the bone space volume determined, in particular automatically, for a path for a needle for administering a bone cement to be determined. The path determined may for example also be employed for the ablation.

For example, the path is determined automatically depending on the data about the bone structure, in particular the computed tomography scan, taking into consideration at least one of the factors including a possible insertion range for the needle, a thickness of a cortical shell for the bone space, a hole in the cortical shell or a distance of the bone space to a plexus venosus posterior. Thus, the path determined may be especially low-risk.

In particular, the path may be determined by ML, (e.g., by an ANN), wherein during training of the ANN the factors mentioned above have been taken into consideration.

This has the advantage that not only the cement volume but also the path may be determined. Thus the intervention may be planned more precisely, and risks reduced further.

One form of embodiment makes provision for a risk of a leakage of the bone cement to be predetermined, wherein the risk is determined by: identifying a hole in a cortical shell of the bone section, which is located closer than a predetermined first distance from the bone space or is connected to the bone space; and/or identifying a region in the cortical shell with a thickness within a predetermined minimum thickness, which region is located closer than a predetermined second distance from the bone space; and/or determining a third distance from the bone space to a plexus venosus posterior.

It may be the case that no hole or more than one hole is identified, which is located closer than the predetermined first distance to the bone space or is connected to the bone space. It may likewise be the case that no region or more than one region is identified, which is located closer than the predetermined second distance to the bone space. The first and second distance may have a predetermined value that is the same or different.

A third distance of the bone space to the plexus venosus posterior may merely be determined when the bone section has such an element.

The risk for the leakage may be determined automatically depending on the data, in particular depending on the computed tomography scan. First of all, an ML, (e.g., a trained ANN), automatically identifies holes, regions, and a plexus venosus posterior in the data or in the computed tomography scan. Subsequently, the respective (first, second, or third) distance may be determined.

Subsequently, a value for the risk of a leakage may be output. Likewise, a warning message may be output, should a limit value for the risk determined be exceeded. Advantageously, this enables the intervention at the patient to be better planned. In particular, treatment measures may be taken into consideration that reduce the risk of the leakage.

A possible point of leakage in the bone section may be identified automatically, e.g., by an ANN. Depending on the possible point of leakage, a path for a needle for injection of a sealing material into the possible point of leakage may be established automatically, e.g., by an ANN. A type and/or a volume of the sealing material may be established automatically, e.g., by an ANN. In particular, the sealing material serves to seal up the possible point of leakage. The intervention at the patient may thus be planned more precisely and advantageously a risk of a leakage reduced.

One form of embodiment makes provision for a risk of a fracture of the bone section to be determined, wherein the risk may be determined by: simulating an introduction of the bone cement with the bone cement volume determined into the bone space of the bone section; simulating a hardening of the simulated introduced bone cement; and determining a force effect on the bone section by the hardened bone cement.

The introduction of the bone cement may be carried out virtually, for example, on the computed tomography scan. As a consequence of the hardening of the bone cement local pressures and stresses may arise, which may affect identified points of contact of the bone cement with the bone section. The force effect of the hardened bone cement on the bone section may be determined automatically.

To determine the risk of the fracture, in particular, the force may be compared with a strength, e.g., with a maximum value for the maximum force effect that may act on the bone section or on the point of contact, so that the bone section does not fracture under the predetermined load.

Based on the risk determined for the fracture, the intervention at the patient may be better planned. In particular, treatment measured may be taken in consideration that reduced the risk of fracture. For example, a bone cement volume may be adjusted in order to reduce the risk.

For application cases or application situations that may be produced with the method and which are not explicitly described here, there may be provision that, in accordance with the method, an error message and/or a request for input of a user response is output and/or a default setting and/or a predetermined initial state is set.

A system for data processing is provided by a further aspect of the disclosure, wherein the system is configured to carry out the acts of the method disclosed herein.

A computer program is provided by a further aspect of the disclosure, including commands that, when the computer program is executed by a computer, cause the computer to carry out the acts of the method.

A storage medium is provided by a further aspect of the disclosure, including commands that, when executed by a computer, cause the computer to carry out the acts of the method.

DETAILED DESCRIPTION

Figure 1:
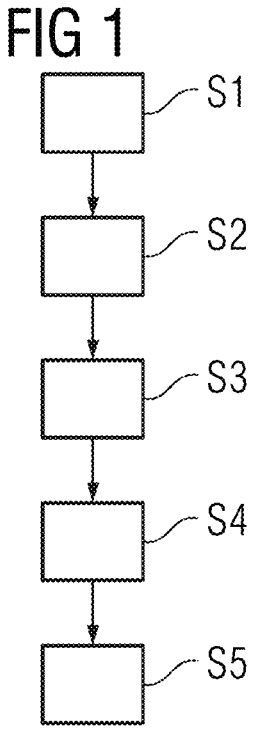
FIG. 1 depicts a flow diagram of a method in accordance with an embodiment.

Shown in FIG. 1 is a flow diagram of a method in accordance with a form of embodiment. For determination of a bone cement volume of a bone cement 10 for a percutaneous vertebroplasty, the method includes the following acts. In act S1, data 1 about a bone structure 3 of a bone section 2 is read in or received. The data 1 read in may include a computed tomography scan 5 of the bone section 2. In act S2, a bone density distribution 13 of the bone section 2 is determined depending on the data 1 that was read in in act S1. In act S3, a bone space 4 in the bone section 2 is determined depending on the bone density distribution 13 determined, wherein a bone density of the bone space 4 is less than a predetermined density threshold value. In act S4, a bone space volume of the bone space 4 determined in act S3 is determined. In act S5, the bone cement volume is determined depending on the bone space volume determined. For example, the bone cement volume determined may correspond to the bone space volume.

Figure 2:
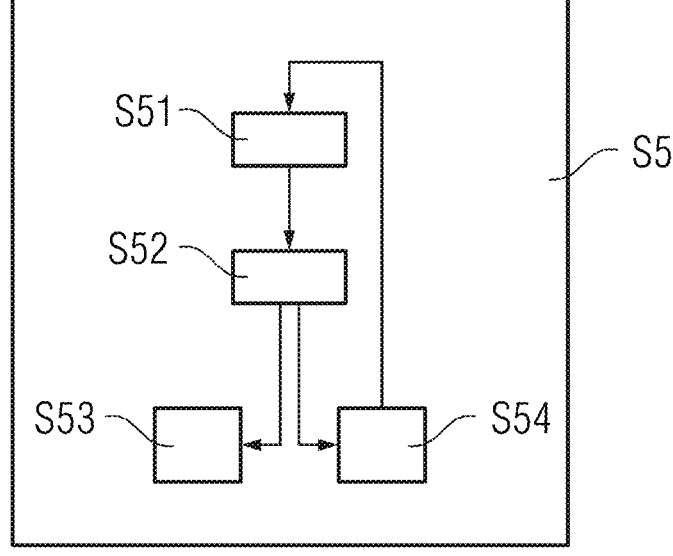
FIG. 2 depicts a flow diagram of an example of a method for determining the bone cement volume.

FIG. 2 shows a flow diagram of a method for determining the bone cement volume in accordance with the fifth act S5. In act S51, the computed tomography scan 5 may be processed by the bone space 4 of the bone section 2 determined being filled virtually, at least in part, with a first volume of the bone cement 10. In act S52, a bone strength of the bone space 4 filled virtually with the first volume of the bone cement may be determined. In act S53, the first volume may be determined as the bone cement volume when the bone strength determined fulfills a condition. If the bone strength does not fulfill the condition, in act S54, the first volume may be adjusted and acts S51 to S54 may be repeated.

Figure 3:
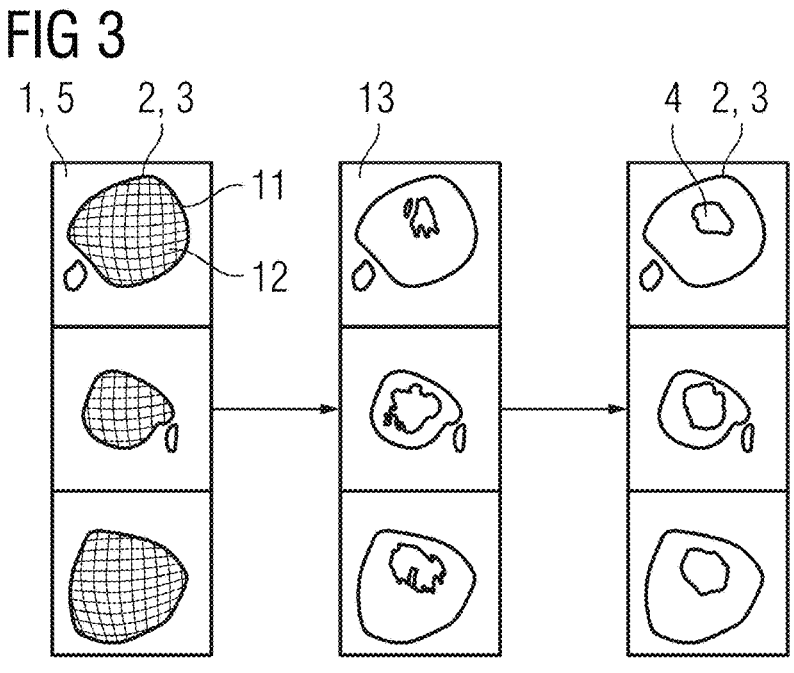
FIG. 3 depicts a schematic diagram of a method in accordance with an embodiment.

Shown in FIG. 3 is a schematic diagram of a method in accordance with a form of embodiment with the aid of three examples arranged below one another. For example, computer-readable data 1, which may include the computed tomography scan 5 of the bone section 2, is read in by a computer (shown on the left). In the example shown, the computed tomography scan 5 is shown as a 2D image. However, the computed tomography scan 5 may be provided and read in as a 3D image. In particular, the computed tomography scan 5 may be high-resolution, corresponding to a 1×1 binning CBCT image 5 and an approximate voxel size of 100 μm. Above all this enables the bone structure 3 of the bone section 2 to be shown in high resolution. In the example shows a cortical shell 11 and a trabecular/sponge-like/porous bone tissue 12 located within the cortical shell 11 may be shown in high resolution. Then, from the computed tomography scan 5, for example, by computation of the volumetric bone density based on a distance transformation, the bone density distribution 13 may be determined. Then, based on the bone density distribution 13 and a predetermined density threshold value, the bone space 4 with a bone density less than the predetermined density threshold value may be determined. Subsequently (not shown here), the bone space volume and the bone cement volume may then be determined.

Figure 4:
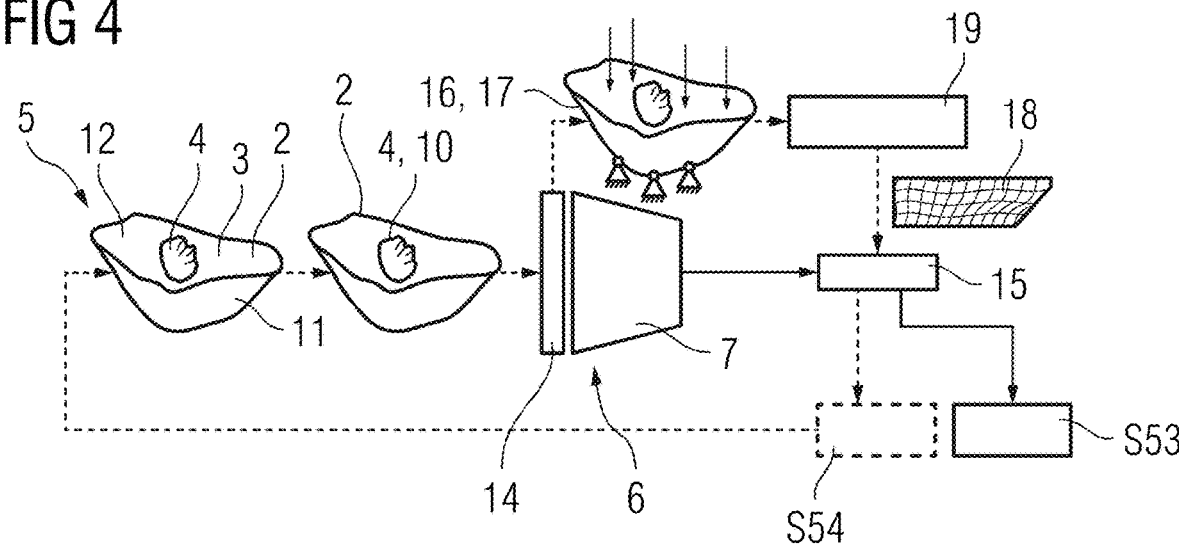
FIG. 4 depicts a schematic diagram of an example of a method for determination of the bone cement volume by a neural network with an encoder architecture.

FIG. 4 shows a schematic diagram of a method for determination of the bone cement volume by an artificial neural network (ANN) 6 with an encoder architecture 7. For example, first of all the computed tomography scan 5 of the bone section 2 is provided. Located in the bone structure 3 is the bone space 4. For example, there may be provision for the computed tomography scan 5 to be changed in that the bone space 4 is subjected to a virtual ablation if this may also be provided in the real treatment. Subsequently, the computed tomography scan 5 may be further changed in that the bone space 4 is virtually filled, at least in part, with in a first volume with bone cement 10. The changed computed tomography scan 5 is now provided as input data to an input 14 of the ANN 6. The ANN 6 may for example have an encoder architecture 7. Then, in particular by the ANN 6, a value 15 of a bone strength may be determined or effectively and reliably computed. If the bone strength fulfills the predetermined condition, for example, by exceeding a predetermined minimum strength value, in accordance with act S53 the first volume may be determined as the bone cement volume.

If the bone strength does not fulfill the predetermined condition, for example, by falling below the predetermined minimum strength value, in accordance with act S54, the method shown in FIG. 4 may be repeated. In particular, the first volume may be changed to do this.

Likewise, shown in FIG. 4 is a training method by which the ANN 6 may be trained. For example, the ANN 6 may be trained by a plurality of computed tomography images 16 of bone parts 17 as input data for the input 14 of the ANN 6 and be trained by a value 15 of the bone strength computed by a simulation 19 as output value. In particular, the bone strength may be computed by a Finite Element Method (FEM) 19. For this, for example, a predetermined, virtual stress, shown by arrows on the bone part 17, for example in the form of forces and/or moments, may be selected as a condition for the FEM computation 19. The solution 18 of the FEM computation 19 may be a stress and/or a strain, or their two- or three-dimensional distribution, so that, based on the solution 18 of the FEM computation 19, the value 15 for the bone strength may be determined.

Figure 5:
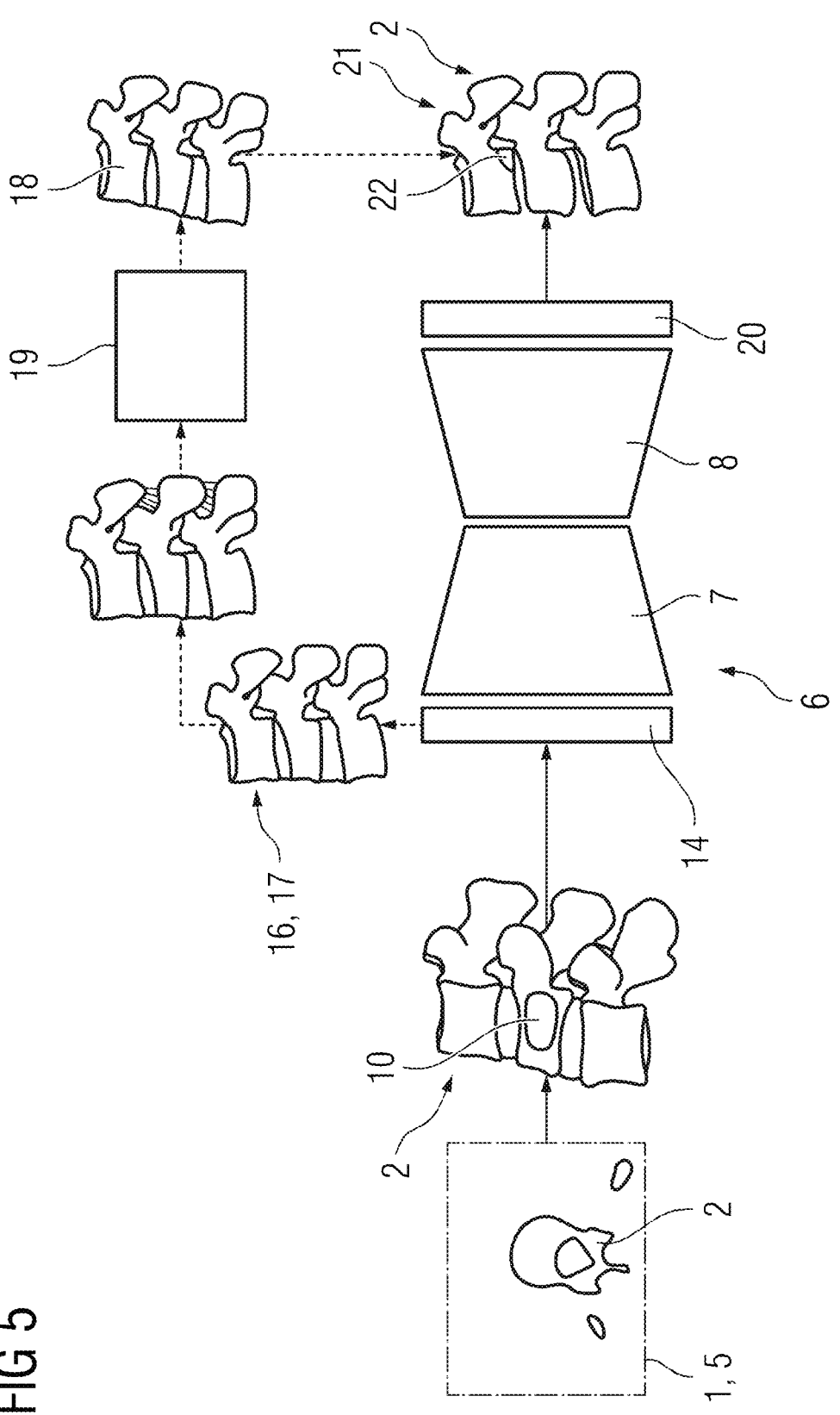
FIG. 5 depicts a schematic diagram of an example of a method for determination of the bone cement volume by a neural network with an encoder-decoder architecture.

FIG. 5 shows a schematic diagram of a method for determination of the bone cement volume by the ANN 6 with an encoder-decoder architecture 7, 8. In accordance with this example, a risk of a fracture of the bone section 2 may be taken into account for the determination of the bone cement volume.

First of all, the computed tomography scan 5 of the bone section 2 may be read in. In the example shown, the bone section 2 includes three neighboring vertebrae of a spinal column, wherein the bone cement 10 is introduced virtually into the central vertebra by changing the computed tomography scan 5. The changed computed tomography scan 5 may serve as input variable for the input 14 of the ANN 6. The ANN 6 in this case may be trained so that, at an output 20, a risk, and in particular due to the encoder-decoder architecture 7, 8, a risk distribution 21, may be determined. In the example shown, in a region 22 of the bone section, in particular in the upper vertebra, an increased risk of a fracture exists. Where necessary, based on the risk distribution determined 21, a bone cement volume or a treatment may be adjusted.

Likewise, shown in FIG. 5 is a training method, by which the ANN 6 may be trained. For example, the ANN 6 may be trained by a plurality of computed tomography images 16 of bone parts 17 as input data for the input 14 of the ANN 6 and by the risk distribution 22 computed by a simulation 19 for the fracture as output value. In particular, a load distribution based on a predetermined stress and based thereon the risk distribution 22 may be computed by a Finite Element Method (FEM) 19. For this, for example, the predetermined stress, shown by arrows on the bone part 17, (e.g., in the form of forces and/or moments), may be selected as the boundary condition. The solution 18 of the FEM computation 19 may be a stress and/or a strain or their two- or three-dimensional distribution so that, based on the solution 18 of the FEM computation 19, the risk distribution 22 of a fracture may be determined.

Figure 6:
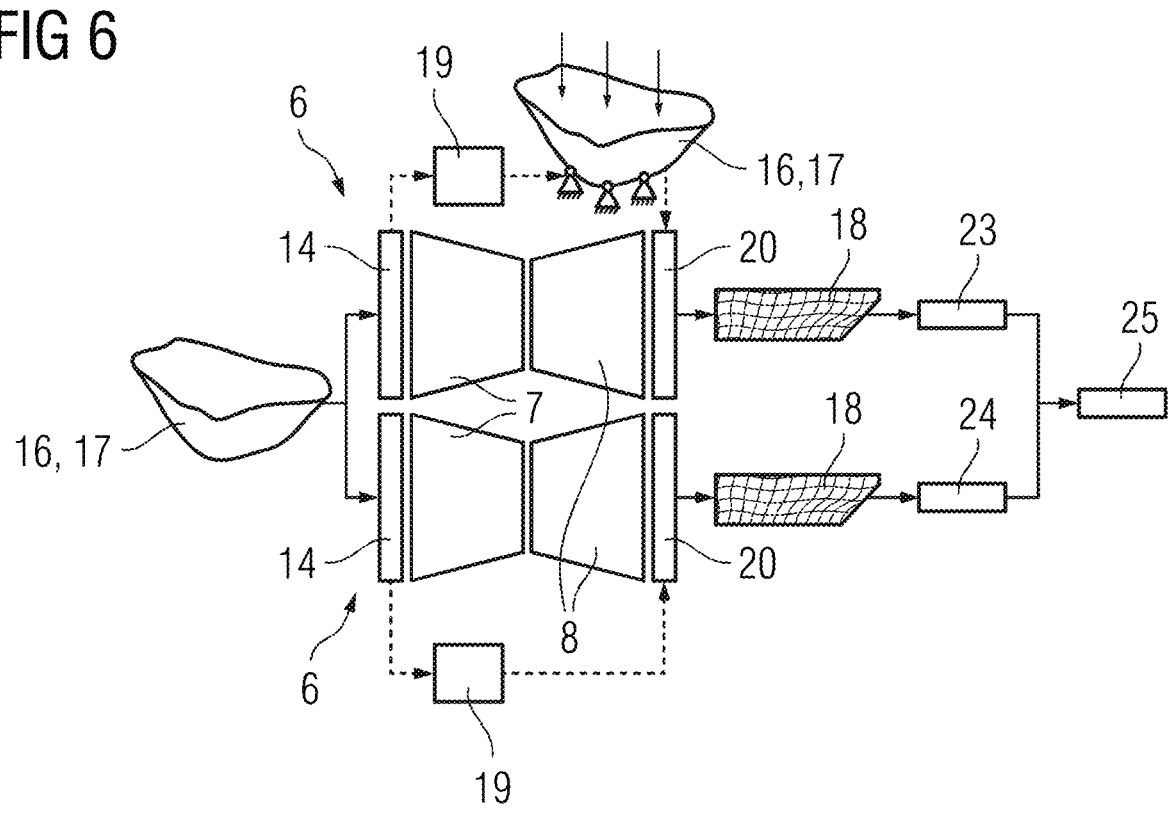
FIG. 6 depicts a schematic diagram of an example of a method for training an artificial neural network with an encoder-decoder architecture.

FIG. 6 shows a schematic diagram of a method for training an ANN 6 with the encoder-decoder architecture 7, 8, wherein the upper ANN 6 is trained in respect of a breaking load 23 and the lower ANN 6 in respect of a breaking moment 24 for determination of a strength value 25 of the bone part 17. First of all, in each case, the plurality of CT images 16 of the bone parts 17 may be provided to the input 14. Likewise the output 20 is provided with the associated numerically computed solution 18 of the plurality of CT images 16 for a stress and/or strain distribution by the simulation 19, so that the respective ANN 6 may be trained.

Figure 7:
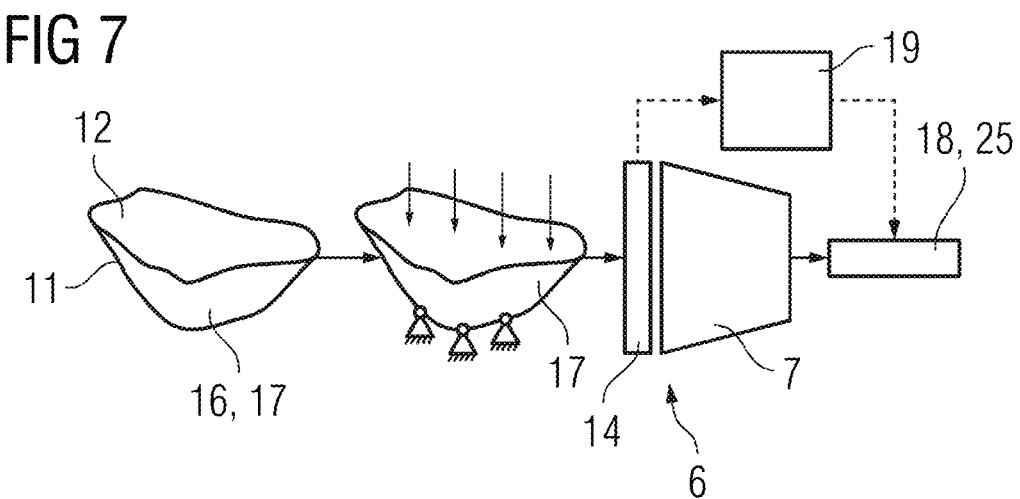
FIG. 7 depicts a schematic diagram of an example of a method for training an artificial neural network with an encoder architecture.

Shown in FIG. 7 is a schematic diagram of method for training the ANN 6 with an encoder architecture 7. For example, not only the plurality of CT images 16 of the bone parts 17, but over and above this also data about a virtual stressing of the plurality of bone parts 17, represented by the plurality of arrows on the bone part 17 serves as the input variable for the input 14. In respect of this virtual stressing of the bone part 17, by the simulation 19, the associated, numerically computed solutions 18, in particular in the form of a solidity value 25, may be determined and provided for the training of the ANN 6.

Figure 8:
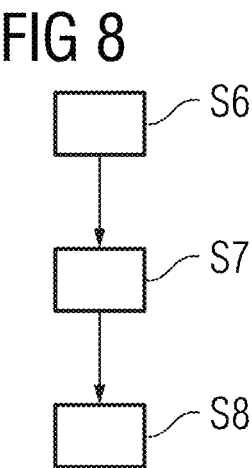
FIG. 8 depicts a flow diagram of an example of a method for determination of a risk of a leakage.

FIG. 8 shows a flow diagram of a method for determination of a risk of a leakage, wherein the risk of the leakage of the bone cement from the bone space is determined beforehand, depending on the following acts. In act S6, a hole in a cortical shell 11 of the bone section 2, which is located closer than a predetermined first distance to the bone space 4 or is connected to the bone space 4, is identified. In act S7, a region in the cortical shell 11 with a thickness below a predetermined minimum thickness is identified, wherein the region is located closer than a predetermined second distance to the bone space. In act S8, a third distance from the bone space 4 to a plexus venosus posterior may be determined.

Figure 9:
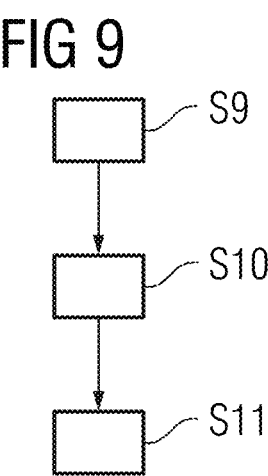
FIG. 9 depicts a flow diagram of an example of a method for determination of a risk of a fracture.

Shown in FIG. 9 is a flow diagram of a method for determination of a risk of a fracture, wherein a risk of the fracture of the bone section is determined, depending on the following acts. In act S9, an introduction of the bone cement with the bone cement volume into the bone space of the bone section may be simulated. In act S10, a hardening of the simulated introduced bone cement may be simulated. In act S11, an effect of a force on the bone section by the hardened bone cement may be determined.

Figure 10:
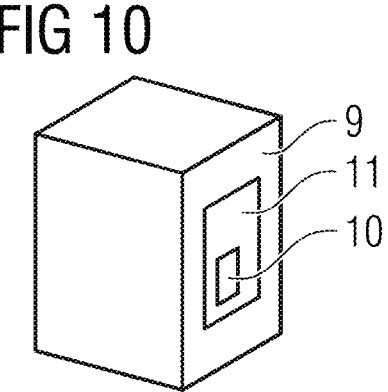
FIG. 10 depicts a schematic diagram of an example of a system for data processing with a computer-readable storage medium and a computer program.

FIG. 10 shows a schematic diagram of a system 9 for data processing with at least one processor, computer-readable storage medium 11, and a computer program 10. For example, the computer program 10 may be stored on or installed on the storage medium 11. For example, the storage medium 11 may be part of the system 9 or be connected to the system 9. The computer program 10 includes commands that, when the computer program is executed by a processor of a computer, for example, the system 9, cause the computer to carry out the acts of the method.

Overall the approach proposed makes possible better results during vertebroplasty in that it provides planning and guidance information from the intraprocedural 3D imaging immediately and in an efficient way.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for determination of a bone cement volume of a bone cement for a percutaneous vertebroplasty, the method comprising:
   receiving data about a bone structure of a bone section;
   determining a bone density distribution of the bone section depending on the data;
   determining a bone space in the bone section depending on the bone density distribution, wherein a bone density of the bone space is less than a predetermined density threshold value;
   determining a bone space volume of the bone space;
   virtually filling at least part of the bone space with a first volume of the bone cement;
   determining a bone strength of the bone space filled virtually with the first volume of the bone cement; and
   determining and outputting the bone cement volume depending on the bone strength.

2. The computer-implemented method of claim 1, wherein the data comprises a computed tomography scan of the bone section.

3. The computer-implemented method of claim 1, wherein the bone cement volume corresponds to the bone space volume.

4. The computer-implemented method of claim 2, wherein the determining of the bone cement volume comprises:
   processing a computer program where the bone space of the bone section is filled virtually, at least in part, with the first volume of the bone cement;
   determining the bone strength of the bone space filled virtually with the first volume of the bone cement;
   determining the first volume as the bone cement volume when the bone strength determined fulfills a condition; and
   adjusting the first volume and repeating the processing of the computer program, the determining of the bone strength, and the determining of the first volume when the bone strength determined does not fulfill the condition.

5. The computer-implemented method of claim 4, wherein the bone strength of the bone space filled virtually with the first volume is determined by machine learning.

6. The computer-implemented method of claim 5, wherein an encoder architecture or an encoder-decoder architecture of an artificial neural network is used in the determination of the bone strength by the machine learning.

7. The computer-implemented method of claim 6, wherein the artificial neural network is trained with a plurality of computed tomography images of bone parts and associated, numerically computed solutions of bone part strengths.

8. The computer-implemented method of claim 4, wherein the condition is fulfilled when the bone strength determined corresponds to or exceeds a predetermined minimum strength value, and wherein the first volume is adjusted by enlarging the first volume.

9. The computer-implemented method of claim 4, wherein the condition is fulfilled when the bone strength determined lies within a predetermined strength range, wherein the first volume is adjusted by reducing the first volume when the bone strength exceeds the predetermined strength range, and wherein the first volume is adjusted by increasing the first volume when the bone strength falls below the predetermined strength range.

10. The computer-implemented method of claim 4, wherein, before the virtual filling, a bone substance in the bone space volume is removed, at least in part, by a virtual ablation.

11. The computer-implemented method of claim 1, wherein, for the determining of the bone space, a plurality of bone elements with a bone density lower than the predetermined density threshold value is determined, and wherein the plurality of bone elements is grouped together into the bone space so that an envelope of the bone space is smoothed and/or convex.

12. The computer-implemented method of claim 1, further comprising:

determining a path for a needle for introduction of a bone cement depending on the bone space volume.

13. The computer-implemented method of claim 1, further comprising:

determining a risk of a fracture of the bone section, wherein the determining of the risk comprises:

simulating an introduction of the bone cement with the bone cement volume determined into the bone space of the bone section;

simulating a hardening of the simulated introduced bone cement; and determining an effect of a force on the bone section by the hardened bone cement.

14. The computer-implemented method of claim 1, wherein the determining of the bone cement volume additionally depends on the bone space volume.

15. A computer-implemented method for determination of a bone cement volume of a bone cement for a percutaneous vertebroplasty, the method comprising:

receiving data about a bone structure of a bone section;

determining a bone density distribution of the bone section depending on the data;

determining a bone space in the bone section depending on the bone density distribution, wherein a bone density of the bone space is less than a predetermined density threshold value;

determining a bone space volume of the bone space;

virtually filling at least part of the bone space with a first volume of the bone cement;

determining a bone strength of the bone space filled virtually with the first volume of the bone cement;

determining and outputting the bone cement volume depending on the bone space volume, the bone strength, or both the bone space volume and the bone strength; and determining a risk of a leakage of the bone cement from the bone space beforehand, wherein the determining of the risk comprises:

identifying a hole in a cortical shell of the bone section that is located closer than a predetermined first distance to the bone space or is connected to the bone space; and/or identifying a region in the cortical shell with a thickness below a predetermined minimum thickness, wherein the region is located closer than a predetermined second distance from the bone space; and/or determining a third distance from the bone space to a plexus *venosus* posterior.

16. A system for data processing, the system comprising:

at least one processor configured to:

receive data about a bone structure of a bone section;

determine a bone density distribution of the bone section depending on the data;

determine a bone space in the bone section depending on the bone density distribution, wherein a bone density of the bone space is less than a predetermined density threshold value;

determine a bone space volume of the bone space;

virtually fill at least part of the bone space with a first volume of a bone cement;

determine a bone strength of the bone space filled virtually with the first volume of the bone cement; and determine and output a bone cement volume depending on the bone strength.

17. The system of claim 16, wherein the determination of the bone cement volume additionally depends on the bone space volume.

\* \* \* \* \*